United States Patent
Calwell

Patent Number: 6,041,503
Date of Patent: Mar. 28, 2000

[54] AROMA THERAPY DELIVERY SYSTEM

[76] Inventor: Stuart Calwell, 854 Edgewood Dr., Charleston, W. Va. 25302

[21] Appl. No.: 09/030,387
[22] Filed: Feb. 25, 1998
[51] Int. Cl.⁷ .................................................. B26B 21/44
[52] U.S. Cl. ................................. 30/41; 30/535; 30/537
[58] Field of Search ............................. 30/41, 535, 537, 30/538

[56] References Cited

U.S. PATENT DOCUMENTS

| | | | |
|---|---|---|---|
| 4,451,984 | 6/1984 | Shimazu | 30/346.52 |
| 4,850,107 | 7/1989 | Valliades et al. | |
| 4,858,314 | 8/1989 | Cunningham | 30/41 X |
| 4,868,982 | 9/1989 | McComas | |
| 4,872,263 | 10/1989 | Etheredge, III | |
| 4,875,287 | 10/1989 | Creasy et al. | |
| 4,974,319 | 12/1990 | Maguire, Jr. et al. | 30/41 |
| 4,998,347 | 3/1991 | Schachter | 30/34.2 |
| 5,005,287 | 4/1991 | Ritter | 30/41 |
| 5,056,221 | 10/1991 | Thoene | 30/41 |
| 5,113,585 | 5/1992 | Rogers et al. | |
| 5,121,541 | 6/1992 | Patrakis | |
| 5,134,775 | 8/1992 | Althaus et al. | |

OTHER PUBLICATIONS

Baron, R., "A Whiff of Reality" *Environment and Behavior*, vol. 26, p. 766 et seq. Nov. 1, 1994.

Primary Examiner—Rinaldi I. Rada
Assistant Examiner—Boyer Ashley
Attorney, Agent, or Firm—Rothwell, Figg, Ernst & Kurz

[57] ABSTRACT

An aroma therapy delivery system is disclosed which incorporates a shaving unit as the delivery vehicle and a water soluble chemical encapsulator as the scent delivery package. The shaving assembly unit may be of a disposable cartridge type adapted for coupling to and uncoupling from a razor handle or may be integral with a handle so that the complete razor is discarded as a unit when the blade or blades become dulled. In either example, the top side of the handle of the shaving unit provides a surface for the affixing of a timed water soluble encapsulated material which comprises varying quantities of scent emitting substances. As the shaving assembly unit is immersed in water during the act of shaving, the particular aroma is released and delivered for the user's olfactory enjoyment.

11 Claims, 5 Drawing Sheets

FIG.3
FIG.4
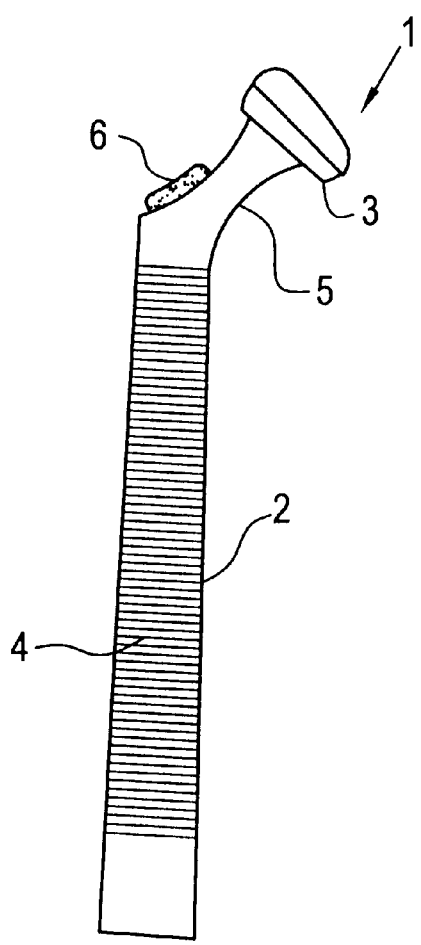
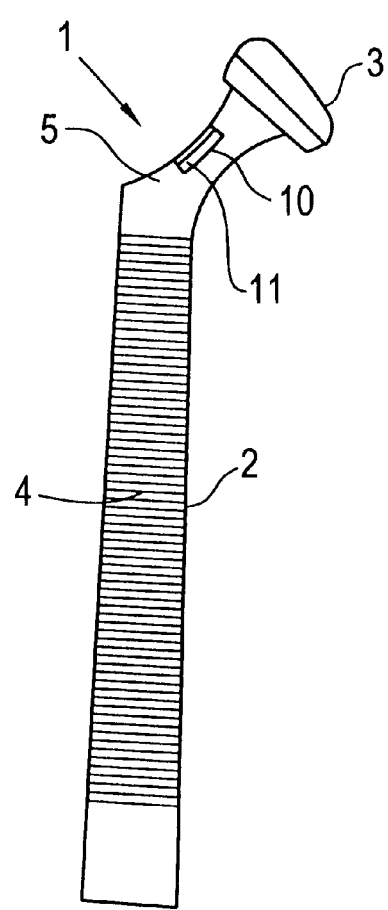

AROMA THERAPY DELIVERY SYSTEM

BACKGROUND OF THE INVENTION

1. Field of the Invention

This invention relates to aroma therapy delivery systems, and more particularly to aroma therapy delivery systems incorporating a shaving unit as the delivery vehicle.

2. Description of the Background Art

Various conventional wet shavers disclose the general concept of applying scented substances to a user's skin as lubricating agents during the shaving process.

For example, U.S. Pat. No. 4,850,107 issued to Valliades et al. on Jul. 25, 1989 discloses a razor assembly with means for intermittently distributing a thin fluid film beneath the bottom of the blade while shaving. The '107 patent discloses an open recessed seating area on the upper, angled portion of the razor shaft for housing a sponge. By applying pressure to the sponge, a thin fluid is released through channels onto the face. The '107 patent teaches that the thin fluid, which may be a scented fluid, may be released on demand to moisten the skin of the user while shaving.

U.S. Pat. No. 4,875,287 issued to Creasy et al. on Oct. 24, 1989 discloses a razor head having a coated surface or substrate which provides, inter alia, a lubricant to the user's face. The '287 patent discloses that the additional materials can be incorporated into the polymer blends such as fragrances.

U.S. Pat. No. 5,134,775 issued to Althaus et al. on Aug. 4, 1992 discloses a shaver head for a wet shaver comprising a device for receiving a liquid shaving preparation which is dispensed during shaving. The '775 patent discloses that the liquid shaving preparation can be perfumed.

U.S. Pat. No. 5,121,541 issued to Patrakis on Jun. 16, 1992 discloses an electric razor comprising a misting mechanism for misting a lubricating agent, such as water, cologne or a beard softener, onto the user's skin while shaving.

While these publications appear to disclose the general concept of using scented lotions or lubricating agents to be applied to a user's face while shaving, they fail to teach an aroma therapy delivery system or aroma therapy delivery systems incorporating a shaving unit as the delivery vehicle which dispense an aroma therapy.

Accordingly, it is the primary object of the present invention to provide a shaver assembly unit which dispenses an aromatic therapy.

It is a further object of the invention to provide a shaver assembly unit that can be easily filled with an aromatic agent.

SUMMARY OF THE INVENTION

In accordance with the present invention, an aroma therapy delivery system comprises a shaving unit as the delivery vehicle and a water soluble chemical encapsulator as the scent delivery package. A timed water soluble encapsulator material, which encloses varying quantities of scent emitting substances, is affixed to an upper side of the shaving assembly unit. When in use, the shaving assembly unit, including the portion of the handle next to the blade holding device, is immersed in water. As the shaving unit is moved about the face, the aroma is delivered to stimulate the user's olfactory senses as the top side of the shaving unit is placed or moves adjacent to the nose or in proximity to it for the purpose of inducing a positive effect on the user's cognitive processes. The aroma encapsulator system is not designed for skin contact but to deliver therapeutic doses of powerful fragrances to the nose to stimulate a positive effect in the brain.

BRIEF DESCRIPTION OF THE DRAWINGS

The above and other objects and advantages of this invention will become more apparent by the following description of invention and the accompanying drawings. Reference numerals in the drawings designate like or corresponding parts throughout same.

FIGS. 2 and 3 are side views of the aroma therapy delivery unit of FIG. 1;

FIG. 4 is a side view of the aroma therapy delivery system in accordance with a second embodiment of the present invention;

DETAILED DESCRIPTION OF THE PREFERRED EMBODIMENTS

The aroma therapy delivery system of the present invention according to a first embodiment is described in connection with FIGS. 1–3 which disclose a shaving unit 1 which serves as the aroma therapy delivery vehicle. Shaving unit 1 comprises a razor handle 2 and a razor head portion 3. In accordance with one embodiment of the invention, the shaving unit 1 can be a disposable cartridge type wherein the razor head portion 3 can be removably coupled and uncoupled to the razor handle 2. In another embodiment, the razor head 3 is integral with the razor handle 2 so that the complete shaving unit 1 is discarded as a unit when the blade or blades become dulled.

Figure 2:
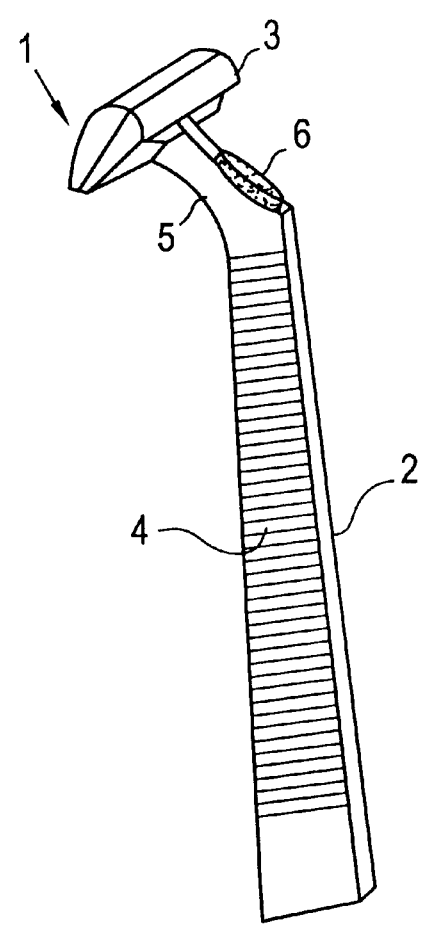

In a preferred embodiment, the razor handle 2 further comprises an angled neck 5 attached to one end of the razor handle 2, as illustrated in FIGS. 2 and 3. The razor head 3 is attached to the other end of the angled neck 5. Also in a preferred embodiment, the razor handle 2 is manufactured to have ridges or protuberances 4 to facilitate better handling of the shaving unit 1.

Figure 1:
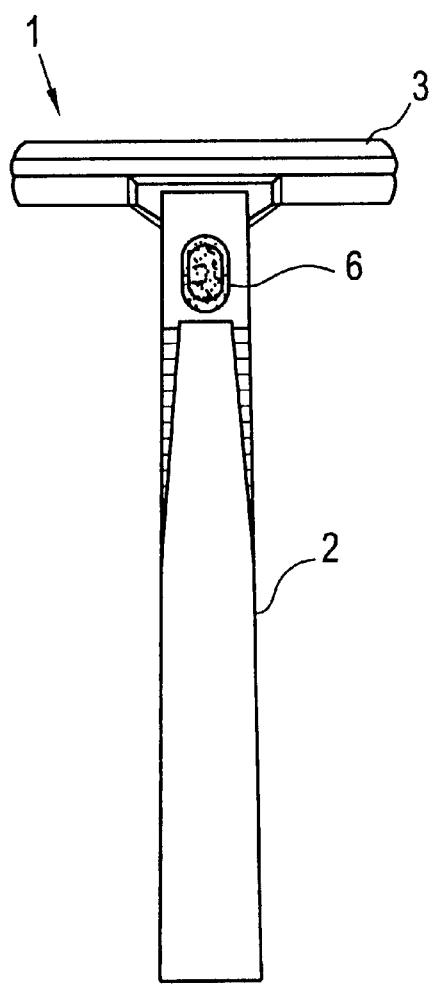
FIG. 1 is a perspective view of the aroma therapy delivery system in accordance with the present invention including a shaving unit which serves as the aroma therapy delivery vehicle.

As further illustrated in FIGS. 1–3, the top side of the razor handle 2 provides a surface for affixing a scent delivery package 6 which comprises a scent emitting substance which, when in close proximity to the nose, delivers therapeutic doses of powerful fragrances to the user. In one embodiment of the invention, the scent delivery package 6 is a water soluble chemical encapsulator which comprises the scented material. The water soluble chemical encapsulator can be manufactured to have a scented material having variety of fragrances such as, for example, fruits, flowers, mint or any other fragrance. The water soluble chemical encapsulator also can be manufactured, by those skilled in the art, having a scented material of varying strengths, depending on the fragrance, sufficient to stimulate a positive effect in the brain.

In a preferred embodiment, the scent delivery package 6 is affixed to the angled neck of the razor handle 2. The scent delivery package 6 can be affixed to the razor handle by any means known to persons skilled in the art such as, for example, an adhesive material. Scent delivery package 6 also could be placed on the razor head 3 or on the razor handle 2.

In an alternative embodiment of the present invention, the handle 2 of the shaving unit 1 has reservoir 10 for containing a scent delivery oil 11, as illustrated in FIG. 4. In a preferred embodiment, the reservoir 10 is constructed as a well in the surface of angled neck portion 5 of handle 2. The reservoir can be of any size capable of housing a scent delivery oil 11 or a scent delivery package 6. For example, the reservoir can be a well measuring approximately 0.25 inches in length, 0.25 inches in width and 0.10 inches in depth. Of course, reservoir 10 can be made larger or smaller depending on the size of the handle 2 and the amount of scent delivery oil 11 or of the scent delivery package 6 being used.

Figure 5:
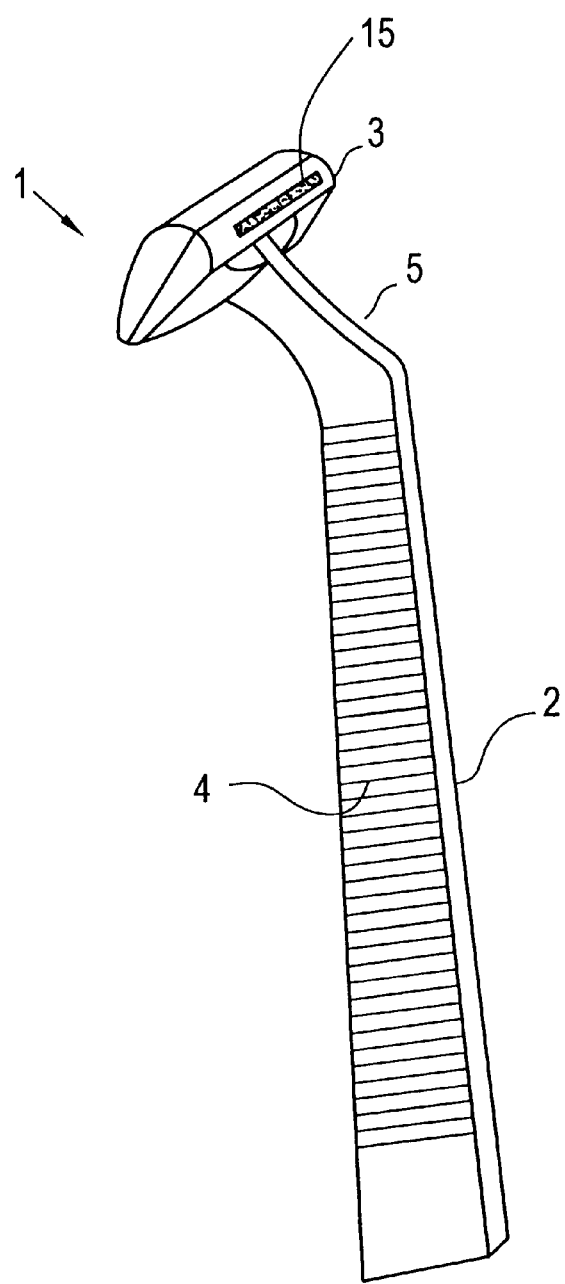
FIG. 5 illustrates the aroma therapy delivery system in accordance with a third embodiment of the present invention.
Figure 6:
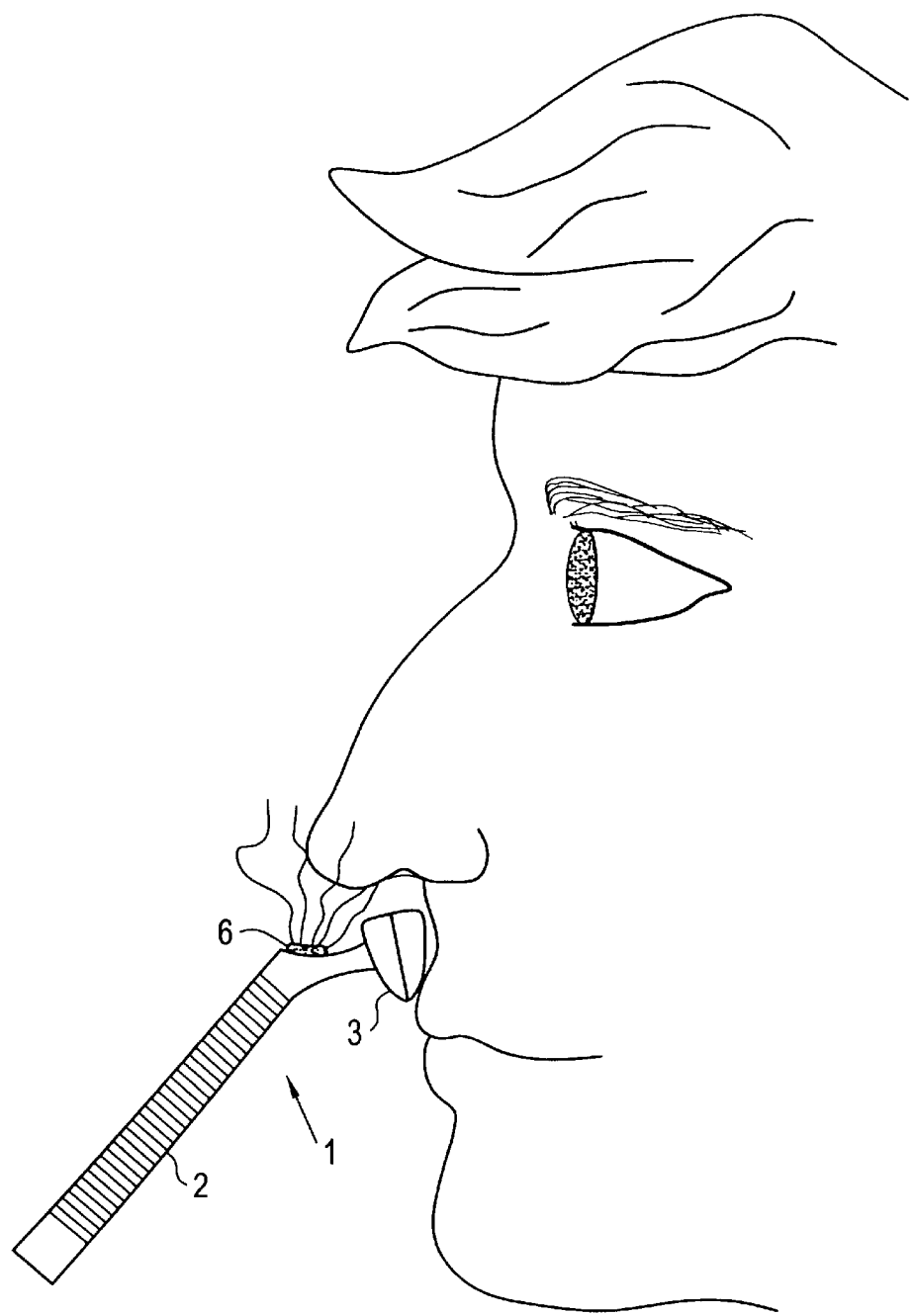
FIG. 6 illustrates the operation of the shaving unit in accordance with the present invention.

In yet another embodiment of the present invention, a scent delivery package 15 is affixed to the top portion of razor head 3, as illustrated in FIG. 5. The scent delivery package 15 is located on the head 3 in a position such that it will not come into contact with the user's skin during the shaving process.

Figure 7:
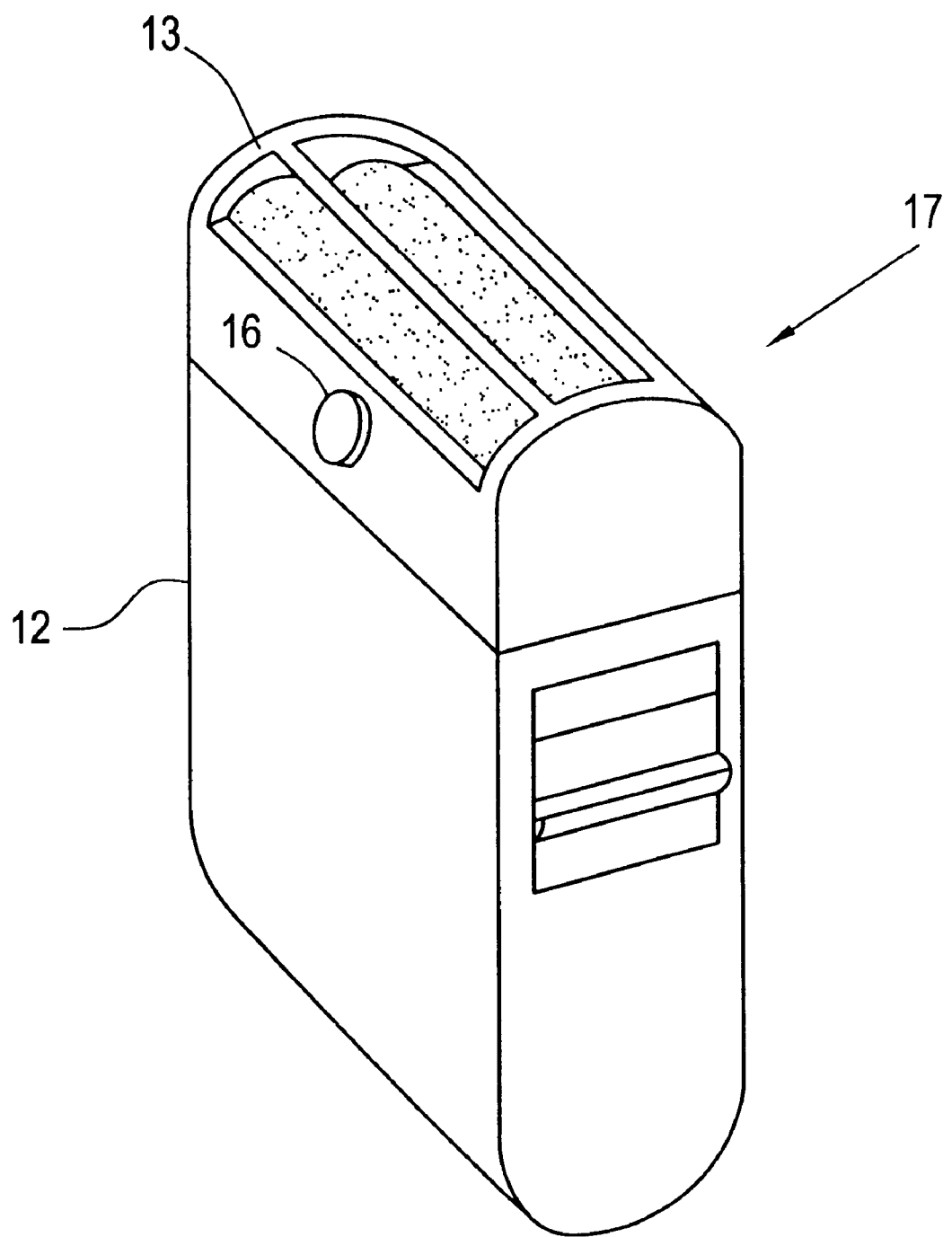
FIG. 7 is a perspective view of the aroma therapy delivery system in accordance with another embodiment of the present invention including an electric shaving unit which serves as the aroma therapy delivery vehicle.

FIG. 7 illustrates the aroma therapy delivery system in accordance with another embodiment of the present invention including an electric shaving unit 17 which serves as the aroma therapy delivery vehicle. Electric shaving unit 17 comprises shaving handle 12, shaving head 13 and scent delivery package 16.

The purpose of this invention is to deliver therapeutic doses of a variety of powerful fragrances to the nose to stimulate a positive effect in the brain. See Baron, Robert, Thomsley, Jill, "A Whiff of Reality . . . ," Vol. 26, *Environment & Behavior*, Nov. 1, 1994, p. 766. This invention does not contemplate any skin contact and has no "shaving purpose." Rather, the shaving unit is merely a unique, convenient vehicle to deliver the beneficial aromas to the olfactory senses. Indeed, shaving is an incidental activity to the delivery of the psychological therapy of having "sense" centers of the brain stimulated for whatever pleasure is derived. For example, a whiff of tangerine in the morning while shaving to lift the spirits or a whiff of peppermint to sharpen the mind are intended to be delivered in a degree of intensity not obtainable or desirable in a general skin contact product. However, the choice of a shaving unit as a vehicle to aid in delivery of these scents carries with it the certainty of daily exposure to the beneficial effects of aromatics, which should add a pleasurable dimension to the act of shaving.

The beneficial fragrances, to be effectively presented for inhalation, can be provided by varying types of chemical packaging. In one embodiment, as described above, microencapsulation provides a means of packaging and storing materials on a microscopic scale for later release under controlled conditions. For example, gelatin encapsulated micro spherical fragrance particles can be prepared by emulsification, gelatin and spray drying, as described generally in U.S. Pat. No. 4,083,798 issued to Vesteeg, and incorporated herein by reference. Controlled release of the aromatic principle can be accomplished by dissolving the particles in water either in a compartment on the shaving unit 1 (as illustrated in FIG. 4), as part of an scent delivery package (as illustrated in FIGS. 1–3) or as an adhesive strip applied to the shaving unit 1 (as illustrated in FIG. 5).

In an alternative embodiment, fragrances can be encapsulated in gelatin/gum arabic, as described in Flores, R. J., Wall, M. D., Carnahan, D. W., Orofin, T. A., *J. Microencapsulation* (1992), 9(3), 298 and incorporated herein by reference, whereby addition of pepsin to the aqueous release solution affects liberation of the fragrance in a manner which can be controlled by temperature, pH and/or pepsin concentration.

Liberation of the fragrance in the shaving unit also may be accomplished from a porous micro spherical carrier as described in Matsukawa, L., Kiritani, M., Miyamoto, A., Japanese Patent No. 52/003,902 to Fuji Film Co., Ltd. (incorporated herein by reference), by application of heat from a non-porous encapsulated polymeric by application of sufficient heat (hot water) to render them porous.

These techniques can be used with any of a variety of well-established microencapsulation technologies employed to control the amount of various fragrances delivered in response to variation in volatility and odor thresholds. The desired scent strength can be accomplished by alteration of the temperature or other physical or chemical characteristics of the delivery environment and appropriate manipulation as known to persons skilled in the art. Depending on the chemical packaging required for a given fragrance, a sufficient quantity of the encapsulated fragrance is applied to the top surface of the shaving unit in a well-defined area, as described above, to maximize presentation to the nose by the user. The area itself may be delineated with a slight raised ridge to provide stability and increase the depth of the chemical packaging.

Thus, while there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. An aroma therapy delivery system for delivering doses of fragrances to the nose of a user comprising:
    (a) a shaving unit, said shaving unit comprising a razor handle and razor head mounted to one end of said razor handle; and
    (b) a scent delivery package mounted on said shaving unit, said scent delivery package being located on said shaving unit that said scent deliver package does not contact the skin of the user when being used.

2. The aroma therapy delivery system of claim 1, wherein said scent delivery package comprises a water soluble chemical encapsulated fragrances.

3. The aroma therapy delivery system of claim 2, wherein said water soluble chemical encapsulated fragrances comprises gelatin encapsulated micro spherical fragrance particles so as to achieve a controlled timed release.

4. The aroma therapy delivery system of claim 2, wherein said water soluble chemical encapsulated fragrances comprises gelatin/gum arabic encapsulated micro-spherical fragrance particles so as to achieve a controlled timed release by manipulation of temperature, pH or pepsin concentration.

5. The aroma therapy delivery system of claim 2, wherein said water soluble chemical encapsulated fragrances comprises non-porous micro spherical carrier particles which are rendered porous by an application of heat.

6. The aroma therapy delivery system of claim 5, wherein said application of heat is from hot water.

7. The aroma therapy delivery system of claim 1, wherein said razor handle comprises a reservoir.

8. The aroma therapy delivery system of claim 7, wherein said scent delivery package is mounted in reservoir on said razor handle.

9. The aroma therapy delivery system of claim 1, wherein said scent delivery package is affixed to said razor head.

10. The aroma therapy delivery system of claim 1, wherein said scent delivery package provides aroma therapy to the user by delivering a powerful scented fragrance for stimulation of the olfactory senses.

11. The aroma therapy delivery system of claim 1, wherein said shaving unit is a wet electric shaver.

\* \* \* \* \*